United States Patent
Mazzoli et al.

(10) Patent No.: US 12,053,565 B2
(45) Date of Patent: *Aug. 6, 2024

(54) BLOOD GAS EXCHANGER WITH RESTRICTION ELEMENT OR ELEMENTS TO REDUCE GAS EXCHANGE

(71) Applicant: Sorin Group Italia S.r.l., Milan (IT)

(72) Inventors: Adriano Mazzoli, San Felice S.P. (IT); Stefano Reggiani, Medolla (IT)

(73) Assignee: Sorin Group Italia S.r.l., Milan (IT)

( * ) Notice: Subject to any disclaimer, the term of this patent is extended or adjusted under 35 U.S.C. 154(b) by 1111 days.

This patent is subject to a terminal disclaimer.

(21) Appl. No.: 16/875,889

(22) Filed: May 15, 2020

(65) Prior Publication Data
US 2020/0276377 A1    Sep. 3, 2020

Related U.S. Application Data

(63) Continuation of application No. 15/571,548, filed as application No. PCT/IB2015/053493 on May 12, 2015, now Pat. No. 10,661,004.

(51) Int. Cl.
*A61M 1/16* (2006.01)
*A61M 1/26* (2006.01)
(Continued)

(52) U.S. Cl.
CPC ............ *A61M 1/1698* (2013.01); *A61M 1/26* (2013.01); *A61M 1/3623* (2022.05);
(Continued)

(58) Field of Classification Search
CPC ...... A61M 1/3698; A61M 1/26; A61M 1/262; A61M 1/267; A61M 1/1678;
(Continued)

(56) References Cited

U.S. PATENT DOCUMENTS

| | | |
|---|---|---|
| 3,339,341 A | 9/1967 | Maxwell et al. |
| 3,957,648 A | 5/1976 | Roget et al. |
| | (Continued) | |

FOREIGN PATENT DOCUMENTS

| | | |
|---|---|---|
| CN | 1042082 A | 5/1990 |
| CN | 1308549 A | 8/2001 |
| | (Continued) | |

OTHER PUBLICATIONS

European Search Report issued in EP Application No. 10161451, dated Sep. 28, 2010, 5 pages.
(Continued)

*Primary Examiner* — Philip R Wiest
(74) *Attorney, Agent, or Firm* — Seager, Tufte & Wickhem LLP

(57) ABSTRACT

Described is a gas exchanger with a restriction element or elements to reduce gas exchange as desired to avoid hypocapnia and hyper-oxygenation in small patients. The gas exchanger includes a gas exchanger housing with an outer wall and a core which defines an inner wall and having a blood inlet for receiving a blood supply and a blood outlet. The gas exchanger also includes: a hollow fiber bundle disposed within the housing between the core and the outer wall; and a gas inlet compartment for receiving an oxygen supply and directing the oxygen supply to first ends of the hollow fiber bundle, wherein the gas inlet compartment includes at least one restriction element configured to allow the oxygen supply to reach only a portion of the hollow fiber bundle.

20 Claims, 8 Drawing Sheets

(51) Int. Cl.
*A61M 1/36* (2006.01)
*B01D 63/02* (2006.01)

(52) U.S. Cl.
CPC ......... *B01D 63/031* (2022.08); *B01D 63/034* (2022.08); *B01D 2313/08* (2013.01); *B01D 2313/19* (2013.01)

(58) Field of Classification Search
CPC . A61M 1/1698; B01D 63/02; B01D 2312/08; B01D 2312/19
See application file for complete search history.

(56) References Cited

U.S. PATENT DOCUMENTS

| | | | |
|---|---|---|---|
| 4,038,190 A | 7/1977 | Baudet et al. | |
| 4,225,439 A | 9/1980 | Spranger | |
| 4,229,305 A | 10/1980 | Fecondini et al. | |
| 4,597,868 A | 7/1986 | Watanabe | |
| 4,639,353 A | 1/1987 | Takemura et al. | |
| 4,707,268 A | 11/1987 | Shah et al. | |
| 4,758,341 A | 7/1988 | Banner | |
| 4,902,476 A | 2/1990 | Gordon et al. | |
| 5,169,530 A | 12/1992 | Shucker et al. | |
| 5,192,439 A | 3/1993 | Roth et al. | |
| 5,192,499 A | 3/1993 | Sakai et al. | |
| 5,270,004 A | 12/1993 | Cosentino et al. | |
| 5,316,724 A | 5/1994 | Mathewson et al. | |
| 5,338,512 A | 8/1994 | Mathewson et al. | |
| 5,514,095 A | 5/1996 | Brightbill et al. | |
| 5,578,267 A | 11/1996 | Cosentino et al. | |
| 5,651,765 A | 7/1997 | Haworth et al. | |
| 5,674,452 A | 10/1997 | Carson et al. | |
| 5,733,398 A | 3/1998 | Carson et al. | |
| 5,762,868 A | 6/1998 | Leonard | |
| 5,762,869 A | 6/1998 | White et al. | |
| 5,817,278 A | 10/1998 | Fini et al. | |
| 5,817,279 A | 10/1998 | Eilers et al. | |
| 5,830,370 A | 11/1998 | Maloney, Jr. et al. | |
| RE36,774 E | 7/2000 | Cosentino et al. | |
| 6,105,664 A | 8/2000 | Gillbrand et al. | |
| 6,113,782 A | 9/2000 | Leonard | |
| 6,241,945 B1 | 6/2001 | Owen | |
| 6,454,999 B1 | 9/2002 | Farhangnia et al. | |
| 6,459,937 B1 | 10/2002 | Morgan et al. | |
| 6,755,894 B2 | 6/2004 | Bikson et al. | |
| 6,960,322 B2 | 11/2005 | Stringer et al. | |
| 7,431,754 B2 | 10/2008 | Ogihara et al. | |
| 7,947,113 B2 | 5/2011 | Ogihara et al. | |
| 7,981,121 B2 | 7/2011 | Stegfeldt et al. | |
| 8,142,546 B2 | 3/2012 | Ogihara et al. | |
| 8,318,092 B2 | 11/2012 | Reggiani et al. | |
| 8,388,566 B2 | 3/2013 | Reggiani et al. | |
| 8,394,049 B2 | 3/2013 | Reggiani et al. | |
| 8,425,838 B2 | 4/2013 | Mizoguchi et al. | |
| 8,652,406 B2 | 2/2014 | Reggiani et al. | |
| 8,685,319 B2 | 4/2014 | Olson et al. | |
| 8,795,220 B2 | 8/2014 | Reggiani et al. | |
| 8,865,067 B2 | 10/2014 | Olson et al. | |
| 8,911,666 B2 | 12/2014 | Mizoguchi et al. | |
| 8,980,176 B2 | 3/2015 | Reggiani et al. | |
| 9,162,022 B2 | 10/2015 | Reggiani et al. | |
| 9,402,943 B2 | 8/2016 | Reggiani et al. | |
| 10,098,994 B2 | 10/2018 | Silvestri et al. | |
| 10,159,777 B2 | 12/2018 | Reggiani et al. | |
| 10,369,262 B2 | 8/2019 | Reggiani | |
| 10,661,004 B2* | 5/2020 | Mazzoli | B01D 63/02 |
| 2002/0039543 A1 | 4/2002 | Ikeda et al. | |
| 2002/0049401 A1 | 4/2002 | Ghelli et al. | |
| 2003/0039582 A1* | 2/2003 | Chambers | A61M 1/1678 96/4 |
| 2003/0080047 A1 | 5/2003 | Watkins et al. | |
| 2003/0175149 A1 | 9/2003 | Searles et al. | |
| 2004/0149645 A1 | 8/2004 | Sunohara et al. | |
| 2004/0175292 A1 | 9/2004 | Ghelli et al. | |
| 2004/0251011 A1 | 12/2004 | Kudo | |
| 2006/0016743 A1 | 1/2006 | Ogihara et al. | |
| 2007/0107884 A1 | 5/2007 | Sirkar et al. | |
| 2007/0166190 A1 | 7/2007 | Ogihara et al. | |
| 2007/0231203 A1 | 10/2007 | Mizoguchi et al. | |
| 2008/0234623 A1 | 9/2008 | Strauss et al. | |
| 2010/0106072 A1* | 4/2010 | Kashefi-Khorasani | A61M 60/37 604/4.01 |
| 2010/0269342 A1 | 10/2010 | Carpenter et al. | |
| 2010/0272606 A1 | 10/2010 | Carpenter et al. | |
| 2010/0272607 A1 | 10/2010 | Carpenter et al. | |
| 2011/0268608 A1 | 11/2011 | Reggiani et al. | |
| 2011/0268609 A1* | 11/2011 | Reggiani | A61M 1/322 422/46 |
| 2012/0046594 A1* | 2/2012 | Reggiani | A61M 1/3667 604/6.13 |
| 2012/0121463 A1 | 5/2012 | Reggiani et al. | |
| 2012/0294761 A1 | 11/2012 | Reggiani et al. | |
| 2013/0142695 A1 | 6/2013 | Reggiani et al. | |
| 2013/0142696 A1 | 6/2013 | Reggiani et al. | |
| 2014/0030146 A1 | 1/2014 | Takeuchi | |
| 2014/0154137 A1* | 6/2014 | Kashefi Khorasani | A61M 60/279 422/46 |
| 2014/0227133 A1 | 8/2014 | Reggiani et al. | |
| 2015/0068670 A1 | 3/2015 | Mizoguchi et al. | |
| 2016/0325036 A1 | 11/2016 | Silvestri et al. | |
| 2016/0354529 A1 | 12/2016 | Reggiani et al. | |
| 2017/0072123 A1 | 3/2017 | Reggiani | |
| 2017/0319767 A1 | 11/2017 | Zaniboni et al. | |
| 2019/0091395 A1 | 3/2019 | Reggiani et al. | |
| 2019/0290821 A1 | 9/2019 | Reggiano | |

FOREIGN PATENT DOCUMENTS

| | | |
|---|---|---|
| CN | 2511309 Y | 9/2002 |
| CN | 2772515 Y | 4/2006 |
| CN | 1907508 A | 2/2007 |
| CN | 1914474 A | 2/2007 |
| CN | 201510571 U | 6/2010 |
| CN | 101837151 A | 9/2010 |
| CN | 201978219 U | 9/2011 |
| CN | 103180032 A | 6/2013 |
| CN | 103328019 A | 9/2013 |
| CN | 103547298 A1 | 1/2014 |
| DE | 19782098 T1 | 11/1999 |
| DE | 102007010112 A1 | 9/2008 |
| DE | 102010027973 A1 | 10/2011 |
| EP | 0312125 | 4/1989 |
| EP | 0170210 B1 | 9/1991 |
| EP | 0582959 A1 | 2/1994 |
| EP | 0895786 A1 | 2/1999 |
| EP | 1108462 A2 | 6/2001 |
| EP | 1180374 A1 | 2/2002 |
| EP | 1371381 A1 | 12/2003 |
| EP | 1618906 B1 | 9/2008 |
| EP | 1834656 B1 | 5/2010 |
| EP | 2524712 A1 | 11/2012 |
| EP | 2537543 A1 | 12/2012 |
| EP | 2420262 B1 | 4/2013 |
| JP | 60053156 A | 3/1985 |
| JP | S61078407 A | 4/1986 |
| JP | S63139562 A | 6/1988 |
| JP | 03169329 A | 7/1991 |
| JP | H042067 B2 | 1/1992 |
| JP | H0439862 B2 | 6/1992 |
| JP | H05177117 A | 7/1993 |
| JP | H11508476 A | 7/1999 |
| JP | 2000501954 A | 2/2000 |
| JP | 3228518 B2 | 11/2001 |
| JP | 2002506692 A | 3/2002 |
| JP | 3284568 B2 | 5/2002 |
| JP | 2002306592 A | 10/2002 |
| JP | 2003520617 A | 7/2003 |
| JP | 2003525736 A | 9/2003 |
| JP | 2006034466 A | 2/2006 |
| JP | 2007190218 A | 8/2007 |

(56) References Cited

FOREIGN PATENT DOCUMENTS

| | | | |
|---|---|---|---|
| JP | 2007244880 A | 9/2007 | |
| JP | 3992377 B2 | 10/2007 | |
| JP | 2007260151 A | 10/2007 | |
| JP | 2007328114 A | 12/2007 | |
| JP | 2009093659 A | 4/2009 | |
| JP | 2011047269 A | 3/2011 | |
| JP | 5020111 B2 | 9/2012 | |
| JP | 2013063121 A | 4/2013 | |
| JP | 2015144857 A | 8/2015 | |
| WO | 1997016213 A2 | 5/1997 | |
| WO | 1997019714 A1 | 6/1997 | |
| WO | 1997033636 A1 | 9/1997 | |
| WO | 9947189 A1 | 9/1999 | |
| WO | 9958171 A2 | 11/1999 | |
| WO | 2010124087 A1 | 10/2010 | |
| WO | 2012066439 A1 | 5/2012 | |
| WO | 2012133372 A1 | 10/2012 | |
| WO | 2015104725 A1 | 7/2015 | |
| WO | 2015107486 A2 | 7/2015 | |
| WO | 2015128886 A1 | 9/2015 | |

OTHER PUBLICATIONS

European Search Report issued in EP Application No. 10173436, dated Feb. 14, 2011, 7 pages.
European Search Report issued in EP Application No. 10186550, dated Jan. 27, 2011, 7 pages.
European Search Report issued in EP Application No. issued in EP Application 10191140, dated Nov. 30, 2011, 8 pages.
European Search Report issued in EP Application No. 12187501, dated Nov. 20, 2013, 6 pages.
European Search Report issued in EP Application No. 13161841, dated Jun. 11, 2013, 6 pages.
International Preliminary Report on Patentability issued in PCT/IB2014/065987, dated May 26, 2017, 9 pages.
International Preliminary Report on Patentability issued in PCT/IB2015/053493, dated Nov. 23, 2017, 9 pages.
International Preliminary Report on Patentability issued in PCT/IT2014/000005, Jul. 12, 2016, 6 pages.
International Preliminary Report on Patentability issued in PCT/IT2014/000058, dated Sep. 6, 2016, 10 pages.
International Search Report and Written Opinion issued in PCT/IB2014/065987, dated Jul. 6, 2015, 10 pages.
International Search Report and Written Opinion issued in PCT/IB2015/053493, dated Jan. 18, 2016, 13 pages.
International Search Report and Written Opinion issued in PCT/IT2014/000005, dated Sep. 26, 2014, 9 pages.
International Search Report and Written Opinion issued in PCT/IT2014/000058, dated Dec. 8, 2014, 14 pages.
International Search Report issued in PCT/IB2011/054725, dated Feb. 9, 2012, 12 pages.
Italian Search Report issued in IT Application No. IT MO20140010, completed Sep. 23, 2014, 7 pages.
European Search Report and Search Opinion Received for EP Application No. 19161228.2, dated Jul. 8, 2019, 7 pages.
International Search Report and Written Opinion issued in PCT/IB2012/052424, dated Oct. 24, 2012, 17 pages.

* cited by examiner

BLOOD GAS EXCHANGER WITH RESTRICTION ELEMENT OR ELEMENTS TO REDUCE GAS EXCHANGE

CROSS-REFERENCE TO RELATED APPLICATION

This application is a continuation of U.S. patent application Ser. No. 15/571,548, filed Nov. 3, 2017, which is a national stage application of PCT/IB62015/053493, filed May 12, 2015, which is herein incorporated by reference in its entirety.

TECHNICAL FIELD

The present disclosure relates generally to extracorporeal fluid circuits. More specifically, the disclosure relates to an oxygenator, or gas exchanger, used in such circuits having at least one restriction element that allows for a reduction in gas exchange to avoid hypo-capnia and hyper-oxygenation in small patients.

BACKGROUND

The disclosure pertains generally to blood processing units used in blood perfusion systems. Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral artery, or other artery.

In small patients, particularly neonatal patients, with low blood volumes, if a standard sized oxygenator is used during cardiopulmonary bypass, excessive carbon dioxide removal and excessive oxygen delivery can result. Excessive carbon dioxide removal can lead to a deleterious change of pH of the blood out of the physiological levels. Avoiding excessive carbon dioxide removal and excessive oxygen delivery is, therefore, desired.

SUMMARY

Example 1 of the present disclosure is a gas exchanger comprising: a gas exchanger housing including an outer wall and a core which defines an inner wall and having a blood inlet for receiving a blood supply and a blood outlet, the gas exchanger housing defining a gas exchanger volume; a hollow fiber bundle disposed within the housing between the core and the outer wall, the hollow fiber bundle comprising hollow gas permeable fibers, each fiber having first and second ends and a hollow interior; and a gas inlet compartment for receiving an oxygen supply and directing the oxygen supply to the first ends of the hollow gas permeable fibers; wherein the gas inlet compartment includes at least one restriction element configured to allow the oxygen supply to reach only a portion of the hollow gas permeable fibers.

Example 2 is the gas exchanger of Example 1, wherein the at least one restriction element comprises a gasket.

Example 3 is the gas exchanger of Example 1, wherein the at least one restriction element is moveable such that the at least one restriction element can assume a first position that is opened in order to allow the oxygen supply to reach all of the hollow gas permeable fibers and a second position that is closed such that the oxygen supply only reaches a portion of the hollow gas permeable fibers.

Example 4 is the gas exchanger of Example 1, wherein the gas exchanger includes at least two restriction elements and the at least two restriction elements are concentrically arranged.

Example 5 is the gas exchanger of Example 1, wherein the gas exchanger housing is tubular in shape, the gas inlet compartment includes a gas inlet that is located at or near the center of the lid, and the at least one restriction element concentrically surrounds the gas inlet.

Example 6 is the gas exchanger of Example 1, wherein 50% of the fiber bundle is provided with oxygen supply for a small, neonatal patient.

Example 7 is a gas exchanger comprising: a gas exchanger housing including an outer wall, at least one lid, and a core which defines an inner wall and having a blood inlet for receiving a blood supply and a blood outlet, the gas exchanger housing defining a gas exchanger volume; a hollow fiber bundle disposed within the housing between the core and the outer wall, the hollow fiber bundle comprising hollow gas permeable fibers, each fiber having first and second ends and a hollow interior, wherein the first ends of the hollow gas permeable fibers are located in a first potting that is located at or near the lid; and a gas inlet compartment including a gas inlet for receiving an oxygen supply and directing the oxygen supply to the first ends of the hollow gas permeable fibers; wherein the gas inlet compartment includes at least one restriction element that concentrically surrounds the gas inlet, wherein the one or more restriction elements are moveable such that the one or more restriction elements can assume a first position that is open in order to allow the oxygen supply to reach all of the first ends of the hollow gas permeable fibers and a second position that is compressed against the potting such that the oxygen supply only reaches a portion of the hollow gas permeable fibers.

Example 8 is the gas exchanger of Example 7, further comprising at least one rigid lever that is connected to the at least one restriction element and that is configured to move the at least one restriction element between the first and second positions.

Example 9 is the gas exchanger of Example 7, wherein the gas inlet compartment is located within the at least one lid.

Example 10 is the gas exchanger of Example 7, wherein the oxygenator includes at least two restriction elements and the at least two restriction elements are concentrically arranged.

Example 11 is the gas exchanger of Example 7 wherein the at least one restriction element comprises a gasket.

Example 12 is the gas exchanger of Example 7, wherein 50% of the fiber bundle is provided with oxygen supply for a small, neonatal patient.

Example 13 is a method of oxygenation comprising: providing a gas exchanger comprising: a gas exchanger housing including an outer wall and a core which defines an inner wall and having a blood inlet for receiving a blood supply and a blood outlet, the gas exchanger housing defining a gas exchanger volume; a gas inlet compartment for receiving an oxygen supply and directing the oxygen supply to the first ends of the hollow gas permeable fibers; wherein the gas inlet compartment includes at least one restriction element configured to allow the oxygen supply to reach only a portion of the hollow gas permeable fibers; activating the at least one restriction element; causing the oxygen supply to flow through the hollow interior of the portion of the hollow gas permeable fibers; delivering blood to the gas exchanger through the blood inlet; causing the blood to flow through the gas exchanger housing over the exterior of the hollow gas permeable fibers; and discharging the blood through the blood outlet.

Example 14 is the method of Example 13, wherein the at least one restriction element comprises a gasket.

Example 15 is the method of Example 13, wherein the at least one restriction element is moveable such that the at least one restriction element can assume a first position that is open in order to allow the oxygen supply to reach all of the hollow gas permeable fibers and a second position that is closed such that the oxygen supply only reaches a portion of the hollow gas permeable fibers.

Example 16 is the method of Example 15, wherein activating the at least one restriction element comprises moving the at least one restriction element to the second position.

Example 17 is the method of Example 13, wherein the gas exchanger includes at least two restriction elements and the at least two restriction elements are concentrically arranged.

Example 18 is the method of Example 13, wherein the gas exchanger housing is tubular in shape, the gas inlet compartment includes a gas inlet that is located at or near the center of the lid, and the at least one restriction element concentrically surrounds the gas inlet.

Example 19 is the method of Example 13, wherein the at least one restriction element concentrically surrounds the gas inlet, wherein the one or more restriction elements are moveable such that the one or more restriction elements can assume a first position that is open in order to allow the oxygen supply to reach all of the first ends of the hollow gas permeable fibers and a second position that is compressed against the potting such that the oxygen supply only reaches a portion of the hollow gas permeable fibers.

Example 20 is the method of Example 13, wherein 50% of the fiber bundle is provided with oxygen supply for a small, neonatal patient.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
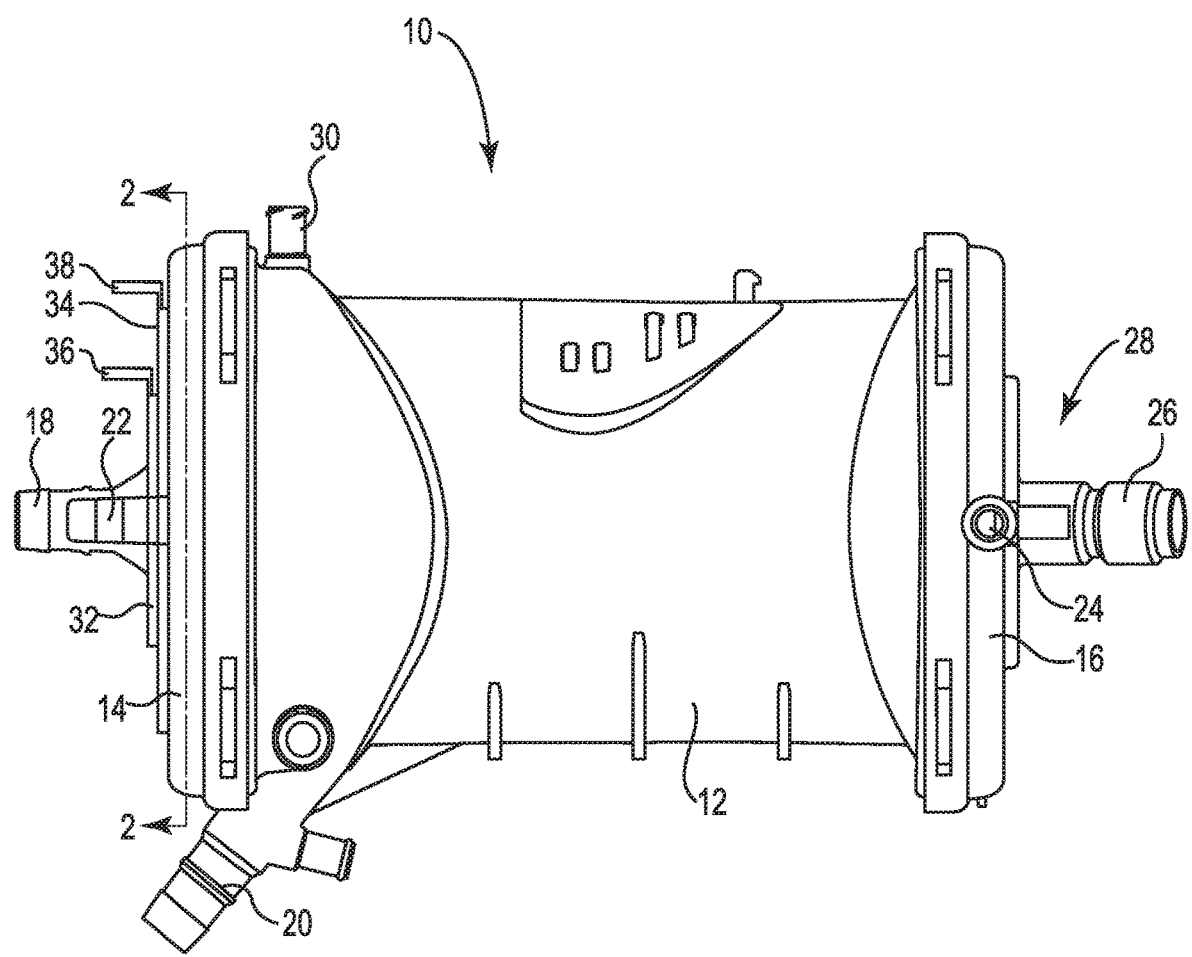
FIG. 1 is a perspective view of an oxygenator, or gas exchanger, in accordance with embodiments of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure.

DETAILED DESCRIPTION

The disclosure pertains to an oxygenator (also commonly referred to as a gas exchanger). In some embodiments, an oxygenator may be used in an extracorporeal blood circuit. An extracorporeal blood circuit, such as may be used in a bypass procedure, may include several different elements such as a heart-lung machine, a blood reservoir, a heat exchanger, as well as an oxygenator. In various embodiments, the gas exchanger, or oxygenator, includes one or more restriction elements that allow for a reduction in gas transfer performance of the oxygenator in order to avoid hypo-capnia and hyper-oxygenation in patients, particularly small or neonatal patients. In various embodiments, one or more restriction elements are configured to be activated to allow an oxygen supply to reach only a portion of hollow gas permeable fibers, thereby reducing the amount of gas exchange performed by the oxygenator.

FIG. 1 is a schematic illustration of an oxygenator 10 (or "gas exchanger"). While the internal components are not visible in the illustration, the oxygenator 10 will include a fiber bundle inside where gas exchange takes place. The oxygenator 10 includes a housing 12, a first end cap 14 that is secured to the housing 12 and a second end cap 16 that is secured to the housing 12. In some embodiments, the housing 12 may include other structures that enable attachment of the housing 12 to other devices. While the housing 12 is largely cylindrical in shape, in some embodiments, the housing 12 may have a triangular, rectangular or other parallelogram cross-sectional shape, for example. The fiber bundle inside may have generally the same sectional shape as the housing 12 or may have a different sectional shape.

In some embodiments, a blood inlet 18 extends into the housing 12 and a blood outlet 20 exits the housing 12. As noted, the oxygenator 10 includes a fiber bundle inside where gas exchange takes place, and thus includes a gas inlet 22 and a gas outlet 24. In some embodiments, the oxygenator 10 may include one or more purge ports 30 that may be used for purging air bubbles from the interior of the oxygenator 10.

The positions of the blood and gas inlets and outlets, and the purge port 30 in FIG. 1 are merely illustrative, as other arrangements and configurations are also contemplated. The purge port 30 may include a valve or a threaded cap. The purge port 30 operates to permit gases (e.g., air bubbles) that exit the blood to be vented or aspirated and removed from the oxygenator 10.

The housing 12 is preferably made of a rigid plastic in order for the oxygenator 10 to be sturdy yet lightweight. The oxygenator is also preferably mainly transparent, in order to allow the user to see through the oxygenator. Therefore, a preferred material for the oxygenator is a transparent, amorphous polymer. One exemplary type of such a material is a polycarbonate, an ABS (Acrylonitrile Butadiene Styrene), or a co-polyester. Other suitable materials for the housing are also contemplated.

The fiber bundle (not shown in FIG. 1) inside housing 12 may include a number or plurality of microporous hollow fibers through which a gas such as oxygen may flow. The blood may flow around and past the hollow fibers. Due to concentration gradients, oxygen may diffuse through the microporous, semi-permeable hollow fibers into the blood while carbon dioxide may diffuse into the hollow fibers and out of the blood.

In some embodiments, the hollow fibers are made of semi-permeable membrane including micropores. Preferably, the fibers comprise polypropylene, polyester, or any other suitable polymer or plastic material. According to various embodiments, the hollow fibers may have an outer diameter of about 0.25 to about 0.3 millimeters. According to other embodiments, the microporous hollow fibers may have a diameter of between about 0.2 and 1.0 millimeters, or more specifically, between about 0.25 and 0.5 millimeters. The hollow fibers may be woven into mats that can range from about 50 to about 200 millimeters in width. In some embodiments, the mats are in a criss-cross configuration. The fiber bundle may be formed of hollow fibers in a variety of winding patterns or structures.

The hollow fibers are embedded, or sealed, at their ends, in rings of polyurethane resin, for example, which is known as "potting." The fiber bundle of hollow fibers is preferably in a cylindrical shape, but other shapes are also contemplated. The hollow fibers, at first ends, are connected to the first end cap 14 through the potting, with the gas inlet 22 being located in the first end cap 14. At second ends, the hollow fibers are connected to the second end cap 16 through the potting with the gas outlet 24 being located in the second end cap 16. The internal lumens of the fibers are part of the gas pathway that is determined by the fist end cap 14, the potting at the first end, the fibers, the second potting and the second end cap 16. The oxygenator chamber is thus defined by the housing as an outer wall and an inner wall or core, together with the pottings at each end of the hollow fibers.

Oxygen, or a mixture of oxygen and air, known as an oxygen supply, enters through gas inlet 22, passes through the microporous hollow fibers within the fiber bundle, and exits the oxygenator 10 through the gas outlet 24. In some embodiments, the pressure or flow rate of oxygen through the oxygenator may be varied in order to achieve a desired diffusion rate of, for example, carbon dioxide diffusing out of the blood and oxygen diffusing into the blood. In some embodiments, as illustrated, the oxygen flows through the hollow fibers while the blood flows around and over the hollow fibers.

Differences in concentration of gases between the blood and the oxygen supply produce a diffusive flow of oxygen toward the blood and of carbon dioxide from the blood in the opposite direction. The carbon dioxide reaches the gas outlet 24 and is discharged from the oxygenator 10.

Any suitable gas supply (or oxygen supply) system may be used with the oxygenator 10 of the disclosure, in order to deliver an oxygen supply to the fiber bundle or hollow fibers of oxygenator 10. Such a gas supply system may also include, for example, flow regulators, flow meters, a gas blender, an oxygen analyzer, a gas filter, and a moisture trap. Other alternative or additional components in the gas supply system are also contemplated.

As shown in FIG. 1, in some embodiments, structural features may be included within oxygenator 10, and specifically within the first end cap 14 in the figure, that allow an oxygen supply delivered to the oxygenator 10 to reach only a portion of the hollow fibers in the fiber bundle where gas exchange takes place. The restriction elements are configured to be either in an open/inactivated position or a closed/activated position. Moving the at least one restriction element to a closed or activated position will result in an oxygen supply being delivered to only a portion of the hollow fibers in the fiber bundle, and thereby will reduce gas transfer performance. The disclosure provides a way to decrease gas exchange efficiency of the oxygenator 10 in order to avoid excessive carbon dioxide removal and excessive oxygen delivery to small patients, including neonatal patients.

FIG. 1 shows two restriction elements, first restriction element 32 and second restriction element 34, extending from or within first end cap 14. Although two restriction elements are shown, it is contemplated that any number of restriction elements may be included, such that the size of the first end cap 14 may accommodate the restriction elements. The figure also shows two levers or arms 36 and 38 that extend from or that are coupled or attached to the restriction elements 32, which are used to move the restriction elements between a restricted or closed configuration and an unrestricted or open configuration. Levers or arms 36, 38 are exemplary structural features used to move the restriction elements 32, 34, but other suitable features are also contemplated by the disclosure.

Figure 2:
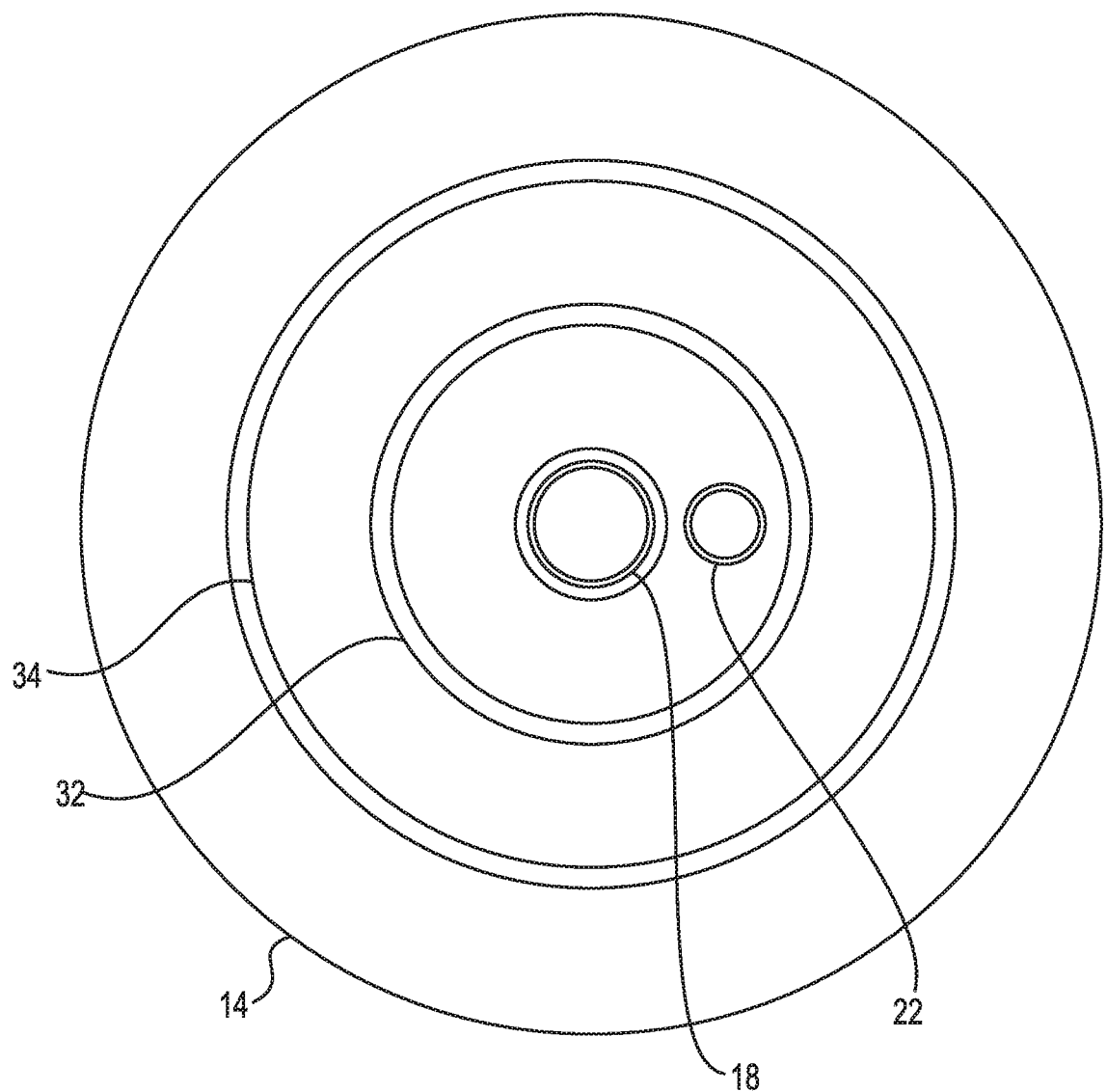
FIG. 2 is a cross-sectional view of the oxygenator of FIG. 1 taken at 2-2.

FIG. 2 is a cross-sectional view of the first end cap 14 shown in the embodiments of the disclosure in FIG. 1 taken at line 2-2. FIG. 2 shows that restriction elements 32 and 34 are circular in shape and are concentrically arranged and surrounding gas inlet 22. The circular shape is one exemplary cross-sectional shape of the restriction elements 32 and 34, but other shapes are also contemplated by the disclosure. The restriction elements 32, 34 may be gaskets, for example, although other options are also contemplated. Preferably, such gaskets may be made from a silicone or any soft rubber-like material that is able to provide an airtight seal with the polymeric wall of the end cap 14. The silicone or rubber-like material of the restriction elements may also be supported by a rigid material in order to provide rigidity to the gasket and allow it to open and close.

Figure 3:
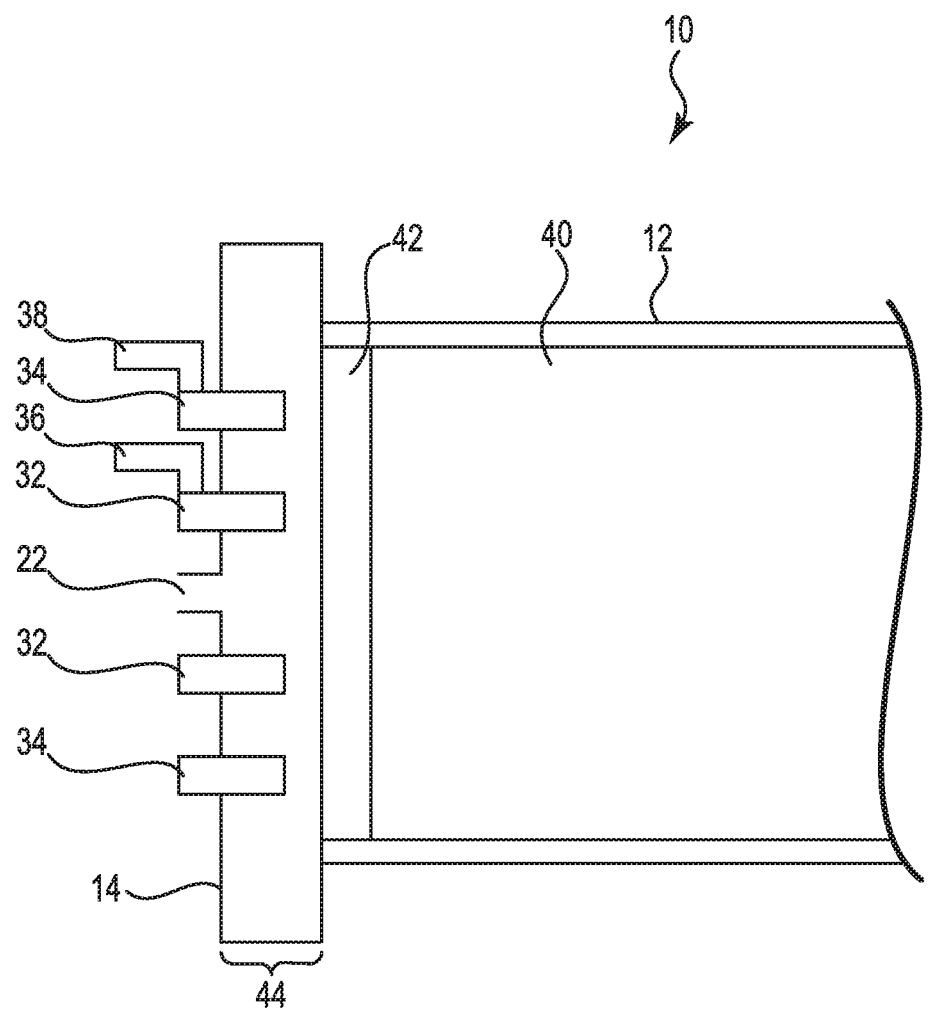
FIG. 3 is a partial cross-sectional view of an oxygenator in accordance with embodiments of the disclosure.
Figure 4:
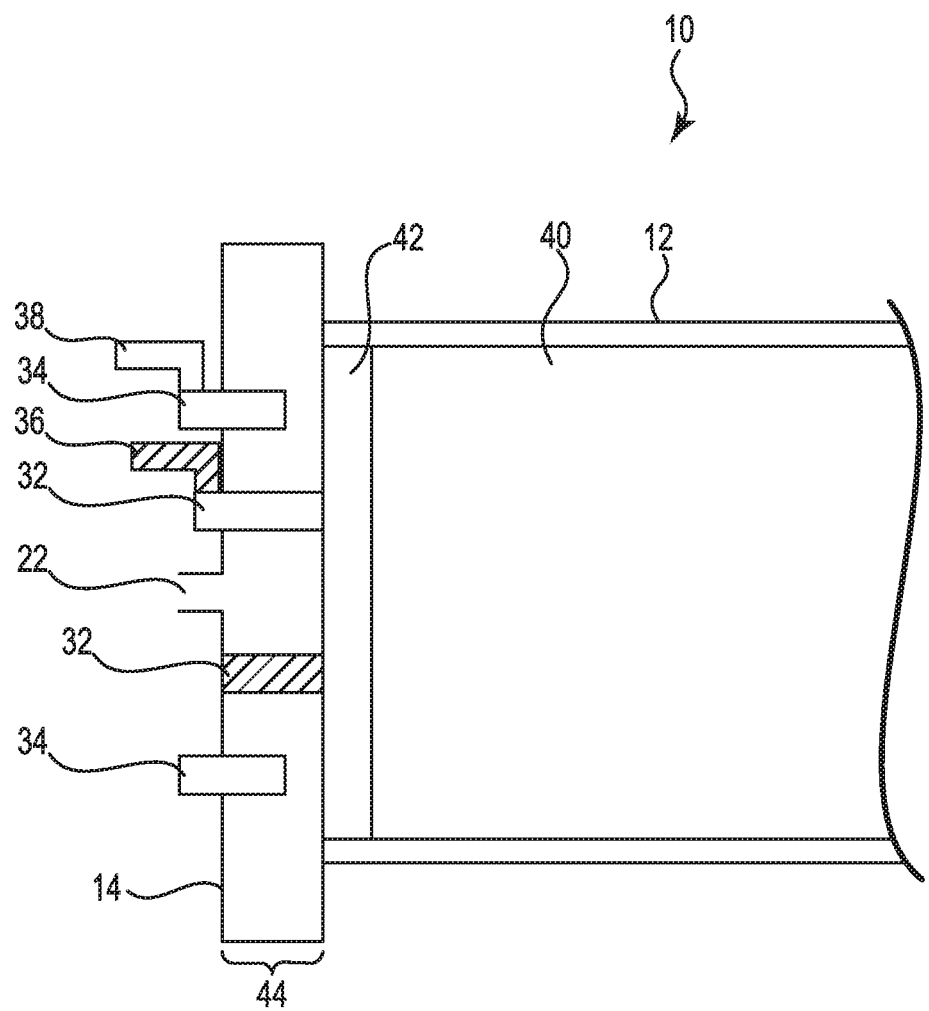
FIG. 4 is a partial cross-sectional view of an oxygenator in accordance with embodiments of the disclosure.
Figure 5:
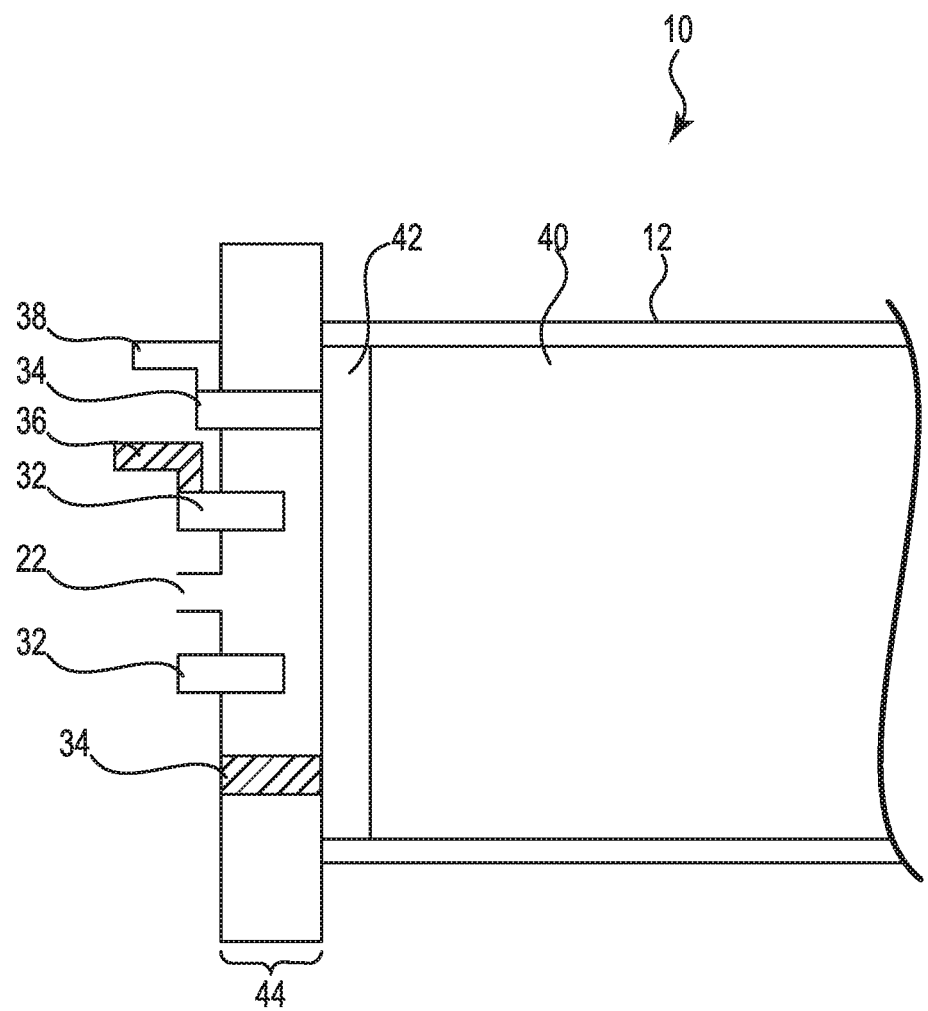
FIG. 5 is a partial cross-sectional view of an oxygenator in accordance with embodiments of the disclosure.

FIGS. 3, 4 and 5 are partial cross-sectional perspective views of oxygenator 10. FIG. 3 shows the oxygenator 10 with both restriction elements 32, 34, in an open or inactivated configuration. FIG. 4 shows the same view as in FIG. 3, but with restriction element 32 being in a closed or activated configuration. FIG. 5 shows the same view again as in FIGS. 3 and 4, but with restriction element 34 being in a closed or activated configuration.

Figure 8A:
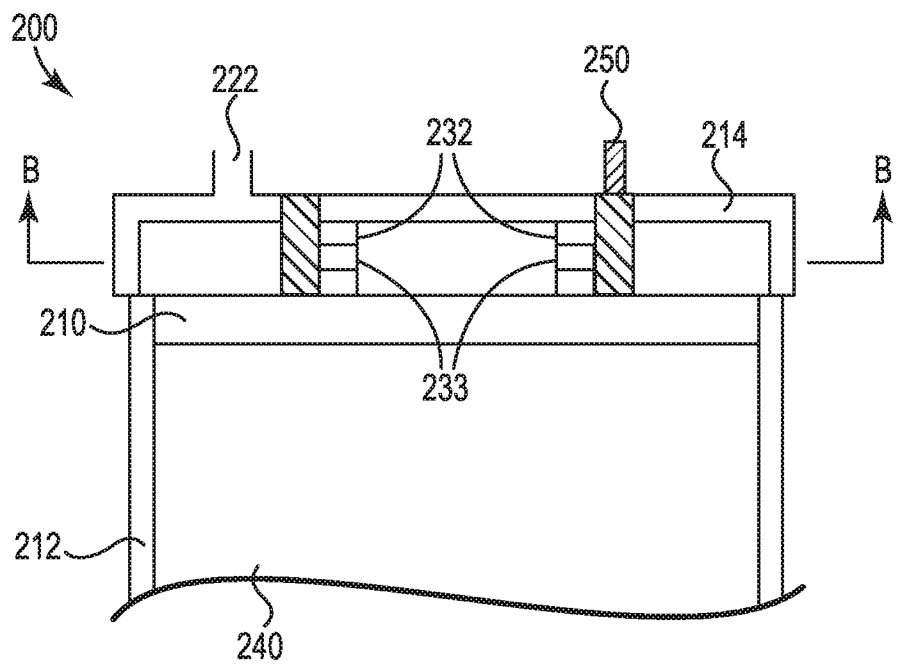
FIG. 8A is a partial cross-sectional view of an oxygenator in accordance with embodiments of the disclosure.
Figure 8B:
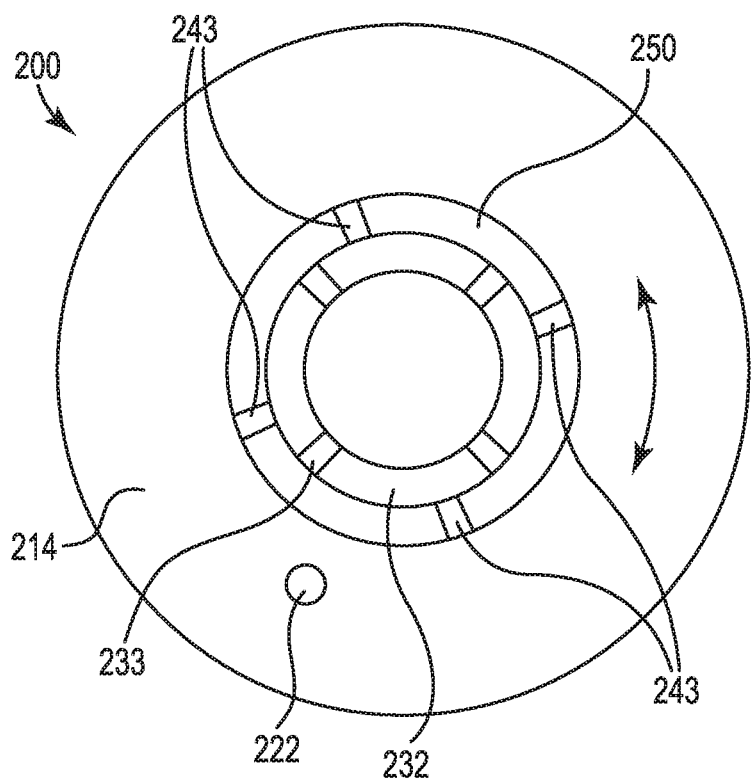
FIG. 8B is a cross-sectional view of the oxygenator of FIG. 8A taken at B-B.

FIGS. 3, 4 and 5 show cross-sectional views of circular-shaped, restriction elements 32, 34, with rigid levers 36, 38 attached, respectively. The levers 36, 38 that are attached to or an extension of restriction elements 32, 34 are one example of a feature that may be used to move the restriction elements between an inactivated configuration and an activated configuration or vice versa. Other methods or structural features that would allow the restriction elements to be moveable between the two configurations are also contemplated by the disclosure. For example, a pre-loaded spring (not shown) may be provided in order to move the restriction elements between an open and a closed position. Alternatively, a snap (not shown) may be used to fix the restriction elements in an open or a closed position. Another alternative restriction element is shown in FIGS. 8A and 8B, and is described in detail below.

Fiber bundle 40, made up of a plurality of hollow fibers (not shown individually), is shown with a potting 42 on first ends of the hollow fibers. A gas inlet compartment 44 is formed within first end cap 14 between the gas inlet 22 and potting 42. The gas-holding capacity or size of the gas inlet compartment 44 is determined by whether the restriction elements 32, 34 are activated or not.

FIG. 4 shows restriction element 32 in the closed or activated configuration. In order to activate the restriction elements 32, 34, the levers 36, 38 may be pushed, which moves the restriction elements 32, 34 inward through the gas inlet compartment 44 and towards potting 42. Once the restriction elements 32, 34 are in contact with potting 42, the portion of the gas inlet compartment 44 that is capable of filling with the gas or oxygen supply is reduced. Also, the portion of the hollow fibers in fiber bundle 40 that are able to be reached by the oxygen supply is reduced. Oxygen supply coming in through gas inlet 22 is only able to reach the portion of the hollow fibers in fiber bundle 40 with first end openings that are located between gas inlet 22 and the activated restriction element 32 or 34. FIG. 5 shows restriction element 34 in an activated configuration. Compared to FIG. 4, where restriction element 32 is activated, a greater number of hollow fibers would be able to receive oxygen supply in the fiber bundle in FIG. 5; however it would still only be only a portion of the hollow fibers in the whole fiber bundle 40. Any number and locations of restriction elements may be included in embodiments of the disclosure, as can be accommodated by the size of the oxygenator 10.

Figure 6:
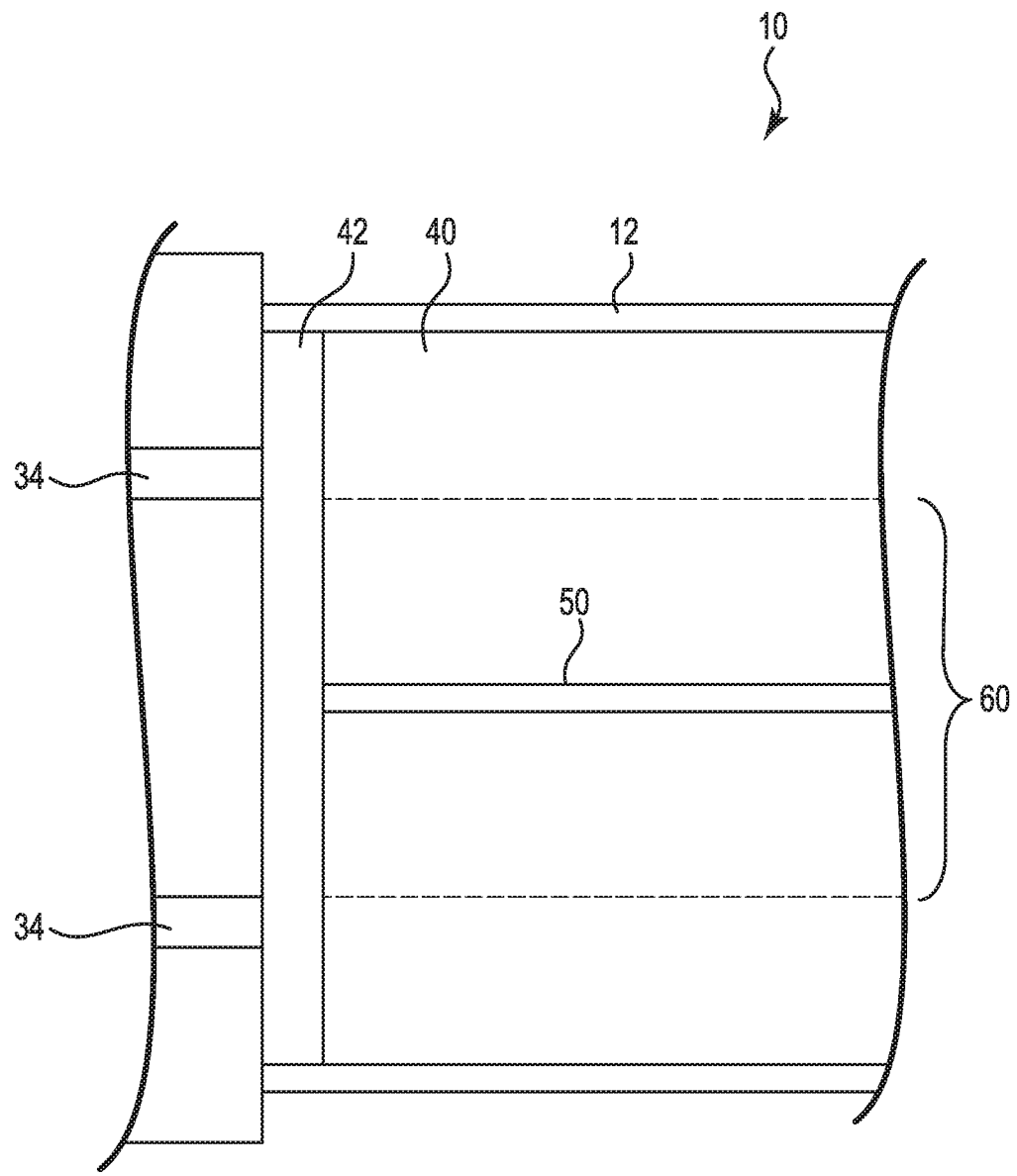
FIG. 6 is a schematic cross-sectional view of an oxygenator in accordance with embodiments of the disclosure.

FIG. 6 is a schematic view of a portion of a cross-section of the oxygenator 10 shown in FIG. 1. The portion shown includes core 50 of the housing 12, which is not shown in previous figures. In FIG. 6, restriction element 34 is activated and in contact with potting 42. Only hollow fibers making up the fiber bundle 40 that are to the interior of the restriction element 34 are active or effective and able to receive oxygen supply. The dotted lines mark the outer perimeter of the active or effective fibers, which are bracketed and marked as 60 in the figure. This configuration is possible if a gas inlet connector (not shown) is to the interior of restriction element 34. If, however, the gas inlet connector (not shown) is to the exterior of the restriction element 34, then the hollow fibers of the fiber bundle that are to the exterior of the restriction element 34 would be active or effective and able to receive oxygen supply.

Figure 7:
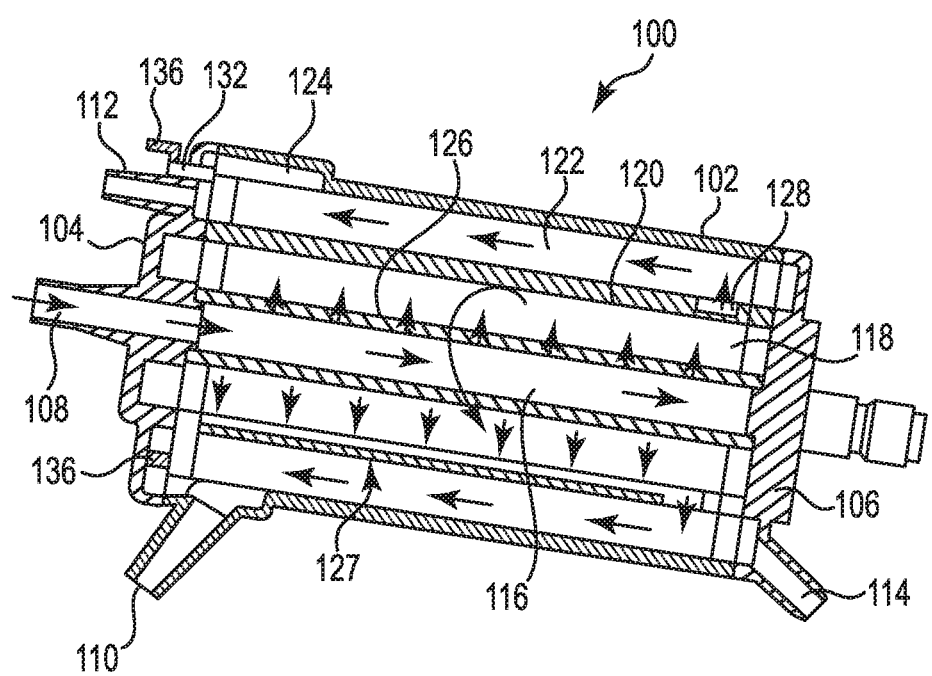
FIG. 7 is a cross-sectional view of an embodiment of an oxygenator in accordance with embodiments of the disclosure.

FIG. 7 is a cross-sectional view of another embodiment of an oxygenator 100 of the present disclosure. The oxygenator of the present disclosure can stand alone or, as shown, oxygenator 100 can include an integrated heat exchanger 118. In the particular embodiment shown, blood flow through the heat exchanger portion 118 is circumferential, while blood flow though the gas exchanger portion is longitudinal. Other arrangements are contemplated, however. As shown in FIG. 7, the oxygenator 100 includes a housing 102, a first end cap 104, and a second end cap 106. The oxygenator 100 includes a blood inlet 108 and a blood outlet 110. A gas inlet 112 permits oxygen to be provided to the gas exchanger portion, while a gas outlet 114 permits gases to exit the oxygenator 100.

The oxygenator 100 includes a heat exchanger core 116, a heat exchanger element 118 disposed about the heat exchanger core 116, a cylindrical shell 120 disposed about the heat exchanger element 118 and a gas exchanger element 122, all disposed inside the outer shell or housing 102. The heat exchanger element 118 and the gas exchanger element 122 may each include a number of hollow fibers as discussed with respect to oxygenator 10 (FIGS. 1-6). In some embodiments, the housing 102 includes an annular portion 124 that is in fluid communication with the blood outlet 110.

In use, blood enters the blood processing apparatus or oxygenator 100 through the blood inlet 108 and passes into the heat exchanger core 116. The blood fills the heat exchanger core 116 and exits through an elongate core aperture 126 and thus enters the heat exchanger element 118. In some embodiments, the heat exchanger core 116 includes a single elongate core aperture 126, while in other embodiments, the heat exchanger core 116 may include two or more elongate core apertures 126. In some embodiments, the elongate aperture 126 allows or directs blood to flow through the heat exchanger element 118 in a circumferential direction.

As shown in FIG. 7, according to some embodiments, the cylindrical shell 120 includes an elongate collector or channel 127. The channel 127 may be disposed at a location substantially diametrically opposed to the location of the elongate core aperture 126. Locating the channel 127 substantially opposite the location of the core aperture 126 causes blood to flow in a generally circumferential flow pattern within the heat exchanger element 118. The channel 127 may extend from between about 1 and about 15 degrees about the circumference of the cylindrical shell 120. In one exemplary embodiment, the channel 127 extends about 5 degrees about the circumference. The blood flow path can be circumferential, as described. Some other alternatives to the blood flow path, however, include radial or longitudinal flow or combinations of circumferential, radial and/or longitudinal flow.

After blood passes through the heat exchanger element 118, it collects in the channel 127 and flows into an annular shell aperture 128. The shell aperture 128, in various embodiments, extends entirely or substantially around the circumference of the cylindrical shell 120, such that blood exits the inner cylindrical shell 120 around the entire or substantially the entire circumference of the cylindrical shell 120. In some embodiments, the radially disposed shell aperture 128 may be located near an end of the oxygenator 100 that is opposite the blood outlet 110, thereby causing the blood to flow through the heat exchanger element 118 in a longitudinal direction. Blood then collects in the annular portion 124 before exiting the oxygenator 100 through the blood outlet 110.

At least one restriction element 132, as in the embodiment shown in FIG. 7, would be located radially outward from, and circumferentially surround, the gas inlet 112. Restriction element 132 would include a lever or another activation member 136 that would allow the restriction element 132 to be moved to contact the potting of the fiber bundle in order to reduce the number of hollow fibers in the fiber bundle of the gas exchanger element 122 that receive oxygen supply.

The embodiment shown in FIG. 7 is one exemplary integrated oxygenator and heat exchanger. The oxygenator of the present disclosure may or may not include a heat exchanger component. Also, other embodiments of integrated oxygenators and heat exchangers are contemplated by the disclosure that may include other configurations and blood flow patterns. The embodiment shown in FIG. 7 is one example.

FIGS. 8A and 8B show two different cross-sections of another embodiment of the gas exchanger, or oxygenator, of the present disclosure. FIG. 8A is a partial cross-section of the gas exchanger 200 taken longitudinally, and FIG. 8B is a cross-section taken at line B-B from FIG. 8A. The oxygenator 200 has a housing 212 surrounding a plurality of hollow fibers 240 (not shown individually). A potting is shown by 210. One end cap 214 is shown that includes a gas inlet 222. A generally circular-shaped restriction element 250 is included in the end cap 214. The restriction element 250 is able to be rotated in two directions as shown by the arrow on FIG. 8B. Restriction element 250 includes a plurality of holes 243 or passages that may be lined up or not lined up with holes or passages 233 in stationary element 232 that may be located either radially inward or outward from restriction element 250. Depending on whether or not the whole fiber bundle or only a portion of the fiber bundle is desired to be used for a particular patient, the holes 243 and 233 may or may not be lined up. If the holes 243 and 233 are lined up then gas will flow through the whole fiber bundle. If the holes 233 and 243 are not lined up, then the gas may only reach the fibers in the portion of the fiber bundle that is located radially outward from the restriction element 250. This is one more exemplary embodiment of the gas exchanger of the present disclosure.

The present disclosure allows the use of one device for a range of sizes of neonatal patients. The device allows for ease in setting appropriate gas exchange performances based on specific patient dimensions, thereby avoiding excess carbon dioxide removal, particularly for very small patients (size 5 kg or less, for example). Gas exchange may be set based on the amount of fiber bundle that is active or used, based on whether or not a restriction element is activated or not. With no restriction elements activated, the percentage of the fiber bundle that is active or used is about 100%. If one restriction element is activated, the percentage of the fiber bundle that is active or used is about 50%, for example. If there are two restriction elements included in the device, then the percentage of active fiber bundle could be either about 33% or about 66%, for example, depending on which restriction element is activated. The percentages of fiber bundle that may be active or used may be varied as well as the number and location of the restriction element or elements.

Another embodiment of the disclosure is a method of oxygenation or oxygenating blood. The steps may comprise providing an oxygenator comprising: an oxygenator housing including an outer wall and a core which defines an inner wall and having a blood inlet for receiving a blood supply and a blood outlet, the oxygenator housing defining an oxygenator volume; a hollow fiber bundle disposed within the housing between the core and the outer wall, the hollow fiber bundle comprising hollow gas permeable fibers, each fiber having first and second ends and a hollow interior; a gas inlet compartment for receiving an oxygen supply and directing the oxygen supply to the first ends of the hollow gas permeable fibers; wherein the gas inlet compartment includes at least one restriction element configured to allow the oxygen supply to reach only a portion of the hollow gas permeable fibers. The oxygenator may alternatively be any embodiment as described, suggested or shown herein, or any other suitable oxygenator. The method may further comprise: activating at least one restriction element; causing an oxygen supply to flow through the hollow interior of the portion of the hollow gas permeable fibers; delivering blood to the oxygenator through the blood inlet; causing the blood to flow through the oxygenation housing over the exterior of the hollow gas permeable fibers; and discharging the blood through the blood outlet. Other methods of oxygenation are also contemplated by the disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A gas exchanger comprising:
a gas exchanger housing including an outer wall and having a blood inlet for receiving a blood supply and a blood outlet;
a hollow fiber bundle disposed within the housing and comprising hollow gas permeable fibers, each hollow gas permeable fiber having first and second ends and a hollow interior; and
a gas inlet compartment for receiving a gas supply including oxygen and directing the gas supply to the first ends of the hollow gas permeable fibers;
wherein the gas inlet compartment includes a gas inlet configured to receive the gas supply; and
at least one restriction element, the at least one restriction element configured to allow the gas supply to reach and flow through only a portion of the hollow gas permeable fibers.

2. The gas exchanger of claim 1, wherein the at least one restriction element is moveable between a first position and a second position.

3. The gas exchanger of claim 2, wherein the gas supply is permitted to reach a first quantity of the hollow gas permeable fibers in the first position, and the gas supply is permitted to reach a second quantity of the hollow gas permeable fibers in the second position, the first quantity being different from the second quantity.

4. The gas exchanger of claim 1, wherein the at least one restriction element surrounds the gas inlet.

5. The gas exchanger of claim 4, wherein the at least one restriction element includes a gasket.

6. The gas exchanger of claim 1, wherein the housing further comprises a purge port configured to purge air bubble from an interior of the housing.

7. The gas exchanger of claim 6, wherein the purge port includes a threaded cap.

8. The gas exchanger of claim 6, wherein the purge port includes a valve.

9. A gas exchanger comprising:
a gas exchanger housing including a blood inlet for receiving a blood supply and a blood outlet;
a hollow fiber bundle disposed within the housing, the hollow fiber bundle including a plurality of hollow gas permeable fibers, each hollow gas permeable fiber having a first end, a second end, and a lumen extending therethrough;
a gas inlet compartment for receiving a gas supply including oxygen; and a restriction element located in the gas inlet compartment, wherein the restriction element is moveable from a first position to a second position, wherein when in the first position, the restriction element allows the gas supply to flow through the lumens of a first portion of the hollow gas permeable fibers and a second portion of the hollow gas permeable fibers, and when in the second position, the restriction element allows the gas supply to flow through the lumens of all the first portion of the hollow gas permeable fibers while preventing the gas supply from flowing through lumens of the second portion of the hollow gas permeable fibers.

10. The gas exchanger of claim 9, wherein the restriction element is moveable only within the gas inlet compartment between the first position and the second position.

11. The gas exchanger of claim 10, wherein the gas supply is permitted to reach a first quantity of the hollow gas permeable fibers in the first position, and the gas supply is permitted to reach a second quantity of the hollow gas permeable fibers in the second position, the first quantity being different from the second quantity.

12. The gas exchanger of claim 9, wherein the restriction element surrounds the gas inlet.

13. The gas exchanger of claim 12, wherein the restriction element includes a gasket.

14. The gas exchanger of claim 9, wherein the blood supply is configured to flow past the first portion of the hollow gas permeable fibers including the gas supply, and the blood supply is configured to flow past the second portion of the hollow gas permeable fibers.

15. A gas exchanger comprising:
a gas exchanger housing including a blood inlet for receiving a blood supply and a blood outlet;
a hollow fiber bundle disposed within the housing, the hollow fiber bundle including a plurality of hollow gas permeable fibers, each hollow gas permeable fiber having a first end, a second end, and a lumen extending therethrough, the first ends of the hollow gas permeable fibers arranged at a first end of the hollow fiber bundle and the second ends of the hollow gas permeable fibers arranged at a second end of the hollow fiber bundle; and
a gas inlet compartment for receiving a gas supply including oxygen;
wherein the gas supply is configured to flow into the lumens of a first portion of the hollow gas permeable fibers at the first end of the hollow fiber bundle while the gas supply is prevented from flowing into the lumens of a second portion of the hollow gas permeable fibers at the first end of the hollow fiber bundle;
wherein the blood supply is configured to flow through the hollow fiber bundle to oxygenate the blood supply.

16. The gas exchanger of claim 15, wherein the gas exchanger housing is configured to direct the blood supply from the blood inlet, past the first portion of the hollow gas permeable fibers including the gas supply, and past the second portion of the hollow gas permeable fibers to the blood outlet.

17. The gas exchanger of claim 15, wherein the housing further comprises a purge port configured to purge air bubble from an interior of the housing.

18. The gas exchanger of claim 17, wherein the purge port includes a threaded cap.

19. The gas exchanger of claim 17, wherein the purge port includes a valve.

20. The gas exchanger of claim 15, further comprising potting at the first end of the hollow fiber bundle and potting at the second end of the hollow fiber bundle, wherein the first ends of both the first and second portions of hollow gas permeable fibers are embedded in the potting at the first end of the hollow fiber bundle, and the second ends of both the first and second portions of hollow gas permeable fibers are embedded in the potting at the second end of the hollow fiber bundle.

* * * * *